United States Patent
Schmidt et al.

(10) Patent No.: US 7,018,685 B2
(45) Date of Patent: Mar. 28, 2006

(54) FLUORINATED AROMATIC COMPOUNDS AND THE USE OF THE SAME IN LIQUID CRYSTAL MIXTURES

(75) Inventors: Wolfgang Schmidt, Dreieich (DE); Rainer Wingen, Hofheim (DE); Barbara Hornung, Hasselroth (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/466,135

(22) PCT Filed: Jan. 10, 2002

(86) PCT No.: PCT/EP02/00191

§ 371 (c)(1), (2), (4) Date: Jan. 26, 2004

(87) PCT Pub. No.: WO02/055463

PCT Pub. Date: Jul. 18, 2002

(65) Prior Publication Data

US 2004/0124399 A1    Jul. 1, 2004

(30) Foreign Application Priority Data

Jan. 11, 2001    (DE) ................................ 101 01 022

(51) Int. Cl.
| | |
|---|---|
| *C09K 19/34* | (2006.01) |
| *C09K 19/32* | (2006.01) |
| *C09K 19/30* | (2006.01) |
| *C07C 23/18* | (2006.01) |
| *C07D 307/91* | (2006.01) |

(52) U.S. Cl. ............. 428/1.1; 252/299.61; 252/299.62; 252/299.63; 544/294; 549/458; 570/187

(58) Field of Classification Search ................ 428/1.1; 252/299.61, 299.62, 299.63; 549/458; 570/187; 544/294; 571/187

See application file for complete search history.

(56) References Cited

U.S. PATENT DOCUMENTS

| 4,367,924 A | 1/1983 | Clark et al. | |
|---|---|---|---|
| 2004/0106798 A1* | 6/2004 | Bremer et al. | ............... 544/294 |

FOREIGN PATENT DOCUMENTS

| DE | 197 20 289 A 1 | | 11/1998 |
|---|---|---|---|
| DE | 10101022 | * | 7/2002 |
| DE | 10115955 | * | 10/2002 |
| EP | 0 032 3620 | | 7/1981 |
| EP | 0 325 035 A 2 | | 7/1989 |
| EP | 1 201 632 A1 | | 5/2002 |
| EP | 1223209 | * | 7/2002 |
| JP | 2001/64216 | * | 3/2001 |
| WO | WO 97/12355 | | 4/1997 |
| WO | WO 99/60441 | | 11/1999 |
| WO | WO 01/10803 A1 | | 2/2001 |

OTHER PUBLICATIONS

English abstract fot JP 2001-64216.*
CAPLUS 1972: 488130.*
CAPLUS 1990: 234935.*
CAPLUS 1995: 798954.*
Database WPI, Section Ch, Week 199846, Derwent Publications Ltd., London, GB; AN 1998-537408, referred to as XP-002192894 & JP 10 236992 A (Chisso Corp.), Sep. 8, 1998.

* cited by examiner

*Primary Examiner*—Shean C. Wu
(74) *Attorney, Agent, or Firm*—Frommer Lawrence & Haug LLP (57) ABSTRACT

The invention relates to fluorinated aromatics of the formula (I)

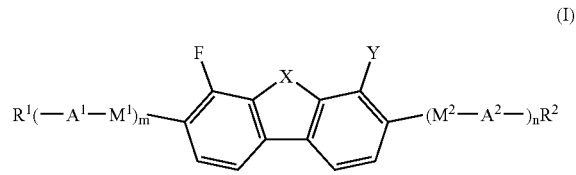

where
X is $CH_2$, $C=O$, $CF_2$, O or S,
Y is H or F, with the proviso that Y has to be F when X is $CH_2$,
and where the other parameters are as defined in claim 1, and also to their use in liquid-crystal mixtures, and also to liquid-crystal mixtures comprising these compounds and to liquid-crystal displays comprising these mixtures.

10 Claims, 1 Drawing Sheet

Fig.1

FLUORINATED AROMATIC COMPOUNDS AND THE USE OF THE SAME IN LIQUID CRYSTAL MIXTURES

Many manufacturers have developed electro-optical displays based on nematic liquid crystals which have been in use for many years, for example in the field of notebook PCs, personal digital assistants and desktop monitors. These use the technologies of TN (twisted nematics), STN (supertwisted nematics), AM-TN (active matrix-twisted nematics), AM-IPS (active matrix-in plane switching), AM-MVA (active matrix-multidomain vertically aligned) which are described in detail in the literature, see, for example, T. Tsukuda, TFT/LCD: Liquid Crystal Displays Addressed by Thin-Film Transistors, Gordon and Breach 1996, ISBN 2-919875-01-9 and literature cited therein; SID Symposium 1997, ISSN-0097-966X, pages 7 to 10, 15 to 18, 47 to 51, 213 to 216, 383 to 386, 397 to 404 and literature cited therein.

Clark and Lagerwall (U.S. Pat. No. 4,367,924) have been able to show that the use of ferroelectric liquid crystals (FLCs) in very thin cells leads to optoelectrical switching or display elements which have response times faster by a factor of up to 1000 compared to the conventional TN (twisted nematic) cells (see, for example, EP-A-0 032 362). As a consequence of these and other favorable properties, for example the possibility of bistable switching and the virtually angle-independent contrast, FLCs are suitable in principle for fields of application such as computer displays and televisions, as demonstrated by a desktop monitor marketed in Japan by Canon since May 1995.

The individual pixels of an LC display are typically arranged in an x,y-matrix formed by the arrangement in each case of a series of electrodes (conductor tracks) along the rows and the columns on the lower or upper side of the display. The points of intersection of the horizontal (row) and vertical (column) electrodes form addressable pixels.

This arrangement of the pixels is customarily referred to as a passive matrix. For addressing, various multiplex schemes have been developed, as described, for example, in Displays 1993, Vol. 14, No. 2, p. 86–93 and Kontakte 1993 (2), p. 3-14. Passive matrix addressing has the advantage of simpler production of the display and associated low production costs, but the disadvantage that passive addressing can only ever be effected line by line, which leads to the addressing time of the entire screen for N lines being N times the line addressing time.

Active matrix technology (AM-LCD) typically combines an unstructured substrate with an active matrix substrate. An electrically nonlinear element, for example a thin-film transistor, is integrated at each pixel of the active matrix substrate. The nonlinear element may also be a diode, metal-insulator-metal or a similar element which is advantageously produced by thin-film processes and is described in the relevant literature, see, for example, T. Tsukuda, TFT/LCD: Liquid Crystal Displays Addressed by Thin-Film Transistors, Gordon and Breach 1996, ISBN 2-919875-01-9 and literature cited therein.

Active matrix LCDs are typically operated using nematic liquid crystals in TN (twisted nematics), ECB (electrically controlled birefringence), VA (vertically aligned) or IPS (in-plane switching) mode. In each case, the active matrix at each pixel generates an electrical field of an individual strength which produces a change in orientation and therefore a change in birefringence which is in turn visible in polarized light. A disadvantage of these processes is currently still the lacking video capability caused by the long switching times of nematic liquid crystals.

For this and other reasons, liquid-crystal displays which are based on a combination of ferroelectric liquid-crystal materials and active matrix elements have also been proposed, see, for example, WO 97/12355, Ferroelectrics 1996, 179, 141–152, or WO 99/60441.

The use of FLCs in electro-optical or fully optical components requires either compounds which form tilted or orthogonal smectic phases and are themselves optically active, or the induction of ferroelectric smectic phases by doping compounds which do form such smectic phases but are not themselves optically active with optically active compounds. The desired phase should be stable over a very wide temperature range.

To achieve a good contrast ratio, a uniform planar alignment of the liquid crystals is necessary. Good alignment in the $S_A$ and $S^*_C$ phase can be achieved, for example, when the phase sequence of the liquid-crystal mixture with decreasing temperature is:

$$\text{isotropic} \rightarrow N^* \rightarrow S_A \rightarrow S^*_C$$

A prerequisite is that the pitch of the helix in the N* phase is very large (greater than 10 μm) or, even better, is fully compensated (see, for example, T. Matsumoto et al., Proc. of the $6^{th}$ Int. Display Research Conf., Japan Display, Sep. 30-Oct. 2, 1986, Tokyo, Japan, p. 468–470; M. Murakami et al., ibid. p. 344–347). This is achieved, for example, by adding one or more optically active dopants which induce a right-handed helix to the chiral liquid-crystal mixture which, in the N* phase, has, for example, a left-handed helix in such amounts that the helix is compensated.

The use of Clark and Lagerwall's SSFLCD effect (surface-stabilized ferroelectric liquid crystal display) for uniform, planar alignment also has the prerequisite that the pitch in the smectic C* phase is significantly greater than the thickness of the display element (Mol. Cryst. Liq. Cryst. 1983, 94, 213 and ibid. 1984, 114, 151).

The optical response time τ[λs] of ferroelectric liquid-crystal systems, which should be as short as possible, depends on the rotational viscosity of the system λ [mPas], the spontaneous polarization Ps [nC/cm²] and the electrical field strength E [V/m], in accordance with the equation $$\tau \sim \frac{\gamma}{Ps \cdot E}$$

Since the field strength E is determined by the electrode separation in the electro-optical component and by the voltage applied, the ferroelectric display medium has to be of low viscosity and/or have a high spontaneous polarization, so that a short response time is achieved.

Finally, in addition to thermal, chemical and photochemical stability, a low optical anisotropy Δn and a small positive or preferably negative dielectric anisotropy Δε are required (see, for example, S. T. Lagerwall et al., "Ferroelectric Liquid Crystals for Displays" SID Symposium, October Meeting 1985, San Diego, Calif., USA).

The totality of these requirements can only be met by mixtures of a plurality of components. The base (or matrix) used preferably comprises compounds which if possible themselves already have the desired phase sequence I→N→$S_A$→$S_C$. Further components of the mixture are often added to reduce the melting point and to broaden the $S_C$ and usually also the N phase, to induce optical activity, for pitch compensation and to vary the optical and dielectric anisotropy, although the rotational viscosity, for example, should if possible not be increased. In addition, it is necessary that the different components have good miscibility with one another within a broad temperature range.

However, since the development of liquid-crystal mixtures can in no way be regarded as complete, the manufacturers of displays are interested in highly differing components for mixtures.

In particular, liquid-crystal mixtures are required which, on the one hand, have a very wide working temperature range and, on the other hand, have a very low threshold voltage, for example for use in automobiles, in which a temperature range of from −40° C. to 100° C. can readily occur, but also for portable devices such as cellphones and notebook PCs.

Furthermore, the trend toward moving pictures using nematic liquid crystals only appears to be realizable if the electrode separation of such LCDs is reduced, since the response times are inversely proportional to the square of the electrode separation. This inevitably results in a reduction of brightness and contrast, unless liquid-crystal mixtures having a high optical anisotropy value (Δn) are used. However, materials having high optical anisotropy usually also have high viscosities and therefore lead away from the objective set. There is therefore a demand for novel, suitable liquid-crystal mixtures and mixture components which have a high clearing point and a high optical anisotropy, while at the same time having comparatively low rotational viscosity.

It is therefore an object of the present invention to provide novel components for use in smectic or nematic liquid-crystal mixtures which have high positive dielectric anisotropy values combined with a favorable relationship of viscosity and clearing point. Furthermore, the compounds should be light- and UV-stable and also thermally stable to a high degree. They should also be suitable for realizing a high voltage holding ratio (VHR). They should also be readily obtainable synthetically and therefore potentially inexpensive.

Derivatives of fluorene and fluorenone for use in liquid-crystalline mixtures have already been disclosed by J. Chem. Soc. 1955, 4359, ibid. 1957, 3228, Pramana Suppl. 1975, 1, 397, Bull. Soc. Chim. Fr. 1975, 2066, Mol. Cryst. Liq. Cryst 1985, 127, 341, ibid. 1985, 129, 17, ibid. 1987, 150B, 361, ibid. 1988, 164, 167, ibid. 1990, 182, 339, DE-A 197 20 289, EP-A 0 113 293, EP-B 0 325 035, JP 05 125055, JP 2000 178211 and EP-A 0 455 219.

JP 10 236992 presents the possibility of constructing, among a multiplicity of other possibilities, a 2,7-disubstituted 3,4,5,6-tetrafluorofluorene derivative or a 3,7-disubstituted 1,2,8,9-tetrafluorodibenzofuran derivative or a 3,7-disubstituted 1,2,8,9-tetrafluorodibenzo-thiophene derivative from the general formula given there, although the application does not go into the synthesis or physical properties of appropriate compounds.

1,8-Difluorofluoren-9-one is disclosed, for example, by Nippon Kagaku Kaishi 1989, 12, 2052–2058 (CAN 1990, 112:234935s), and 1-fluorofluoren-9-one, for example, by Chem. Ind. 1961, 179–180. However, it is not possible therefrom to discern suitability of these molecules or of their derivatives as part of a component of liquid-crystal mixtures.

It has now been found that compounds of the formula (I)

(I)

where
X is $CH_2$, C=O, $CF_2$, O or S,
Y is H or F, with the proviso that Y is F when X is $CH_2$,
$R^1$ and $R^2$ are the same or different and are each hydrogen, or are a straight-chain or branched alkyl radical having from 1 to 16 carbon atoms or a straight-chain or branched alkenyl radical having from 2 to 16 carbon atoms where
a) one or more nonadjacent and nonterminal $CH_2$ groups may be replaced by —O—, —C(=O)O—, —O—C(=O)—, —O—C(=O)—O—, —C(=O)— or —Si($CH_3$)$_2$—, and/or
b) one $CH_2$ group may be replaced by —C≡C—, cyclopropane-1,2-diyl or cyclobutane-1,3-diyl, and/or
c) one or more hydrogen atoms may be replaced by F or Cl, and/or
d) the terminal $CH_3$ group may be replaced by one of the following chiral groups (optically active or racemic):

where $R^3$ is a straight-chain or branched alkyl radical having from 1 to 12 carbon atoms or a straight-chain or branched alkenyl radical having from 2 to 12 carbon atoms, in each of which one or more nonadjacent and nonterminal $CH_2$ groups may be replaced by —O— and/or one or more hydrogen atoms may be replaced by F or Cl, with the proviso that only one of $R^1$ and $R^2$ may be hydrogen,
$M^1$ and $M^2$ are the same or different and are each —C(=O)—O—, —O—C(=O)—, —$CH_2$—O—, —O—$CH_2$—, —$CF_2$—O—, —O—$CF_2$—, —CH=CH—, —CF=CF—, —C≡C—, —$CH_2$—$CH_2$—C(=O)—O—, —O—C(=O)—$CH_2$—$CH_2$—, —$CH_2$—$CH_2$—, —$CF_2$—$CF_2$—, —($CH_2$)$_4$— or a single bond,
$A^1$ and $A^2$ are the same or different and are each 1,4-phenylene where one or two hydrogen atoms may be replaced by F, Cl or CN, pyridine-2,5-diyl where one hydrogen atom may be replaced by F, pyrimidine-2,5-diyl, 1,4-cyclohexylene where one or two hydrogen atoms may be replaced by $CH_3$ or F, 1-cyclohexene-1,4-diyl where one hydrogen atom may be replaced by $CH_3$ or F, or 1,3-dioxane-2,5-diyl,
m and n are each independently 0 or 1, but in total not greater than 1, fulfill these requirements in an exceptional manner.

When there are replacements at a plurality of the positions specified, they are each independently selected from the replacements specified and may therefore be the same or different. There may therefore also be a plurality of different replacements among those specified at different positions in the compound at the same time.

Preference is given to the compounds of the formula (I) where

X is $CH_2$, $C{=}O$ or O, $R^1$ and $R^2$ are the same or different and are each a straight-chain or branched alkyl radical having from 1 to 14 carbon atoms or a straight-chain or branched alkenyl radical having from 2 to 14 carbon atoms, in each of which one or more nonadjacent and nonterminal $CH_2$ groups may be replaced by —O— and/or one or more hydrogen atoms may be replaced by F,

$R^3$ is a straight-chain or branched alkyl radical having from 1 to 10 carbon atoms where one nonterminal $CH_2$ group may be replaced by —O—,

$M^1$ and $M^2$ are the same or different and are each —$CH_2$—O—, —O—$CH_2$—, —$CH_2$—$CH_2$— or a single bond,

$A^1$ and $A^2$ are the same or different and are each 1,4-phenylene where one or two hydrogen atoms may be replaced by F, or 1,4-cyclohexylene, and m and n are each independently 0 or 1, but in total not greater than 1.

Particular preference is given to the following compounds of the formulae (I a) to (I q)

(Ia)

(Ib)

(Ic)

(Id)

(Ie)

-continued

(If)

(Ig)

(Ih)

(Ii)

(Ik)

(Il)

(Im)

(In)

(Io)

(Ip)

-continued (Iq)

where
R⁴ and R⁵ are the same or different and are each a straight-chain alkyl, alkenyl or alkoxy radical having from 2 to 12 carbon atoms.

Very particular preference is given to compounds of the formulae (I a), (I b), (I c), (I i), (I k) and (I I) where
R⁴ and R⁵ are the same or different and are each a straight-chain alkyl, alkenyl or alkoxy radical having from 2 to 10 carbon atoms.

The provision of compounds of the formula (I) considerably enlarges the range of liquid-crystalline substances in a quite general sense which are suitable in different respects relating to application for preparing liquid-crystalline mixtures.

In this context, the compounds of the formula (I) have a wide range of application. Depending on the choice of substituents, they may be added to other classes of compound, in order, for example, to influence the dielectric and/or optical anisotropy of such a dielectric. They may also serve to optimize its threshold voltage and/or its viscosity.

The compounds of the formula (I) are particularly suitable, even in small added amounts, to influence the dielectric anisotropy ($\Delta\epsilon$) in the direction of higher negative values.

The invention therefore provides not only compounds of the formula (I) but also the use of these compounds as components of liquid-crystalline mixtures.

The compounds of the formula (I) may be used in liquid-crystal mixtures. In the case of nematic mixtures, they are particularly suitable for "Active Matrix Displays" (AM-LCD) (see, for example, C. Prince, Seminar Lecture Notes, Volume 1, p. M-3/3-M-22, SID International Symposium 1997, B. B: Bahadur, Liquid Crystal Applications and Uses, Vol. 1, p. 410, World Scientific Publishing, 1990, E. Lüder, Recent Progress of AMLCD's, Proceedings of the 15ᵗʰ International Display Research Conference, 1995, p. 9–12) and "in-plane-switching displays" (IPS-LCD), and, in the case of smectic liquid-crystal mixtures, for tilted smectic (ferroelectric or antiferroelectric) displays. In the case of ferroelectric mixtures, the compounds of the formula (I) according to the invention are suitable in particular for use in displays which are operated in inverse mode (see, for example, J. C. Jones, M. J. Towler, J. R. Hughes, Displays 1993, 14, No. 2, 86–93; M. Koden, Ferroelectrics 1996, 179, 121–129).

Further components of liquid-crystal mixtures which comprise compounds of the formula (1) according to the invention are preferably selected from the known compounds having smectic and/or nematic and/or cholesteric phases. Mixture components suitable for this purpose are listed in particular in WO 00/36054, WO 97/04039, DE-A-195 31 165 and EP-A-0 893 424, which are explicitly incorporated herein by way of reference.

The invention also provides liquid-crystal mixtures which comprise at least one compound of the formula (I), preferably in an amount of from 1 to 40% by weight, based on the liquid-crystal mixture. The mixtures preferably comprise at least 3 further components or (liquid-crystalline) compounds. The invention additionally provides electro-optical display elements (liquid-crystal displays) which comprise the mixtures according to the invention. Preference is given to liquid-crystal displays which comprise the nematic or smectic (ferroelectric or antiferroelectric) mixtures according to the invention in combination with active matrix elements.

Preference is likewise given to liquid-crystal displays which comprise the ferroelectric liquid-crystal mixtures according to the invention and are operated in the inverse or $\tau V_{(min)}$ mode.

The displays according to the invention are typically constructed in such a way that a liquid-crystal layer is enclosed on both sides by layers which are typically, in this sequence starting from the LC layer, at least one alignment layer, electrodes and a boundary sheet (e.g. of glass). They may additionally comprise spacers, adhesive frames, polarizers and, for color displays, thin color-filter layers. Further possible components are antireflection, passivation, compensation and barrier layers and also electrically nonlinear elements, such as thin-film transistors (TFTs) and metal-insulator-metal (MIM) elements. The construction of liquid-crystal displays has already been detailed in relevant monographs (see, for example, E. Kaneko, "Liquid Crystal TV Displays: Principles and Applications of Liquid Crystal Displays", KTK Scientific Publishers, 1987).

The switching characteristics of an FLC device can generally be represented by a diagram in which the driving voltage (V) is plotted horizontally and the width of the addressing pulses ($\tau$, time) vertically (see, for example, J. C. Jones, M. J. Towler, J. R. Hughes, Displays 1993, 14, No. 2, 86–93, diag. 4, 8, 10 and 11). A switching curve is determined experimentally and divides the V,$\tau$ area into a switching and nonswitching region. The pulsewidth typically shortens with increasing voltage. This behavior characterizes the normal mode (see, for example, Jones, diag. 4). However, in the case of suitable materials, the V$\tau$ curve exhibits a minimum (at the voltage $V_{(min)}$), as can be seen, for example, in Jones in diagrams 8, 10 and 11. This minimum arises from superposition of dielectric and ferroelectric twisting. FLC devices are operated in inverse mode when the sum of the row and column driving voltages in the working temperature range is higher than the minimum on the V$\tau$ curve, i.e. $V_{(row)}+V_{(column)}>V_{(min)}$.

Possible synthetic routes to compounds of the formula (I) are shown by way of example in the schemes 1 to 7 which follow, although other processes are also conceivable and possible.

The following abbreviations are used:

| | |
|---|---|
| n-BuLi | n-butyllithium |
| DCC | dicyclohexylcarbodiimide |
| DEAD | diethyl azodicarboxylate |
| DMAP | 4-(dimethylamino)pyridine |
| DME | dimethoxyethane |
| DMF | N,N-dimethylformamide |
| KOtBu | potassium tert-butoxide |
| LiTMP | lithium 2,2,6,6-tetramethylpiperidide |
| MTBE | tert-butyl methyl ether |
| 4-TsOH | 4-toluenesulfonic acid |

Scheme 1 a) $H_2SO_4/H_2O$ b) polyphosphoric acid c) $KMnO_4$
d) 1. $SOCl_2$ 2. $NH_3$  e) $NaOBr/H_2O$
f) 1. $NaNO_2/HCl/H_2O$ 2. $HBF_4/H_2O$ 3. Δ  g) $Et_3SiH/CF_3COOH$ 1,8-Difluorofluorene is obtained by reduction of 1,8-difluorofluoren-9-one [127375-32-0] with triethylsilane (in a similar manner to WO 89/02425). 1,8-Difluorofluoren-9-one is synthesized as described in Nippon Kagaku Kaishi 1989, 12, 2052 and Yamaguchi Daigaku Kogakubu Kenkyu Hokoku 1995, 45, 281 (Scheme 1). Commercially available 9,9-bis(2-cyanoethyl)fluorene (9,9-fluorenedipropionitrile [4425-97-2]; prepared by Michael addition of acrylonitrile to fluorene) is hydrolyzed, and the resulting fluorene-9,9-dipropanoic acid [4425-95-0] (see also J. Org. Chem. 1968, 33,2575) is cyclized with polyphosphoric acid to give 1,2,11,12-tetrahydro-3H,10H-benzo[hi]fluoranthene-3,10-dione [98804-54-7]. Oxidation affords 9-oxofluorene-1,8-dicarboxylic acid [94024-99-4], which is converted via the corresponding carbonyl chloride to 9-oxofluorene-1,8-dicarboxamide [127375-28-4] (general procedure: Organikum, VEB Deutscher Verlag der Wissenschaften, 15$^{th}$ ed., Berlin 1984, Ch. 7.1.5.4 and 7.1.5.2). Hofmann degradation (general procedure: ibid., Ch. 9.1.2.1) affords 1,8-diaminofluoren-9-one [127375-29-5] which [lacuna] converts to the corresponding bis(diazonium tetrafluoroborate) and affords 1,8-difluorofluoren-9-one [127375-32-0] by thermal decomposition according to Balz-Schiemann (see also J. Am. Chem. Soc. 1974, 96, 3536).

1,8-Difluorofluoren-9-one can also be prepared in a similar manner from fluorene-1,8-dicarboxylic acid [88830-26-6] (prepared by acylating fluorenone with dimethylcarbamoyl chloride according to Ref. Zh., Khim. 1983, Abstr. No. 16Zh185) instead of 9-oxofluorene-1,8-dicarboxylic acid (Scheme 2).

Scheme 2

Dibenzofuran-4,6-dicarboxylic acid [88818-47-7] and dibenzofuran-4-carboxylic acid [2786-05-2] (obtained by carboxylating dibenzofuran: Tetrahedron: Asymmetry 1999, 10, 2417; J. Am. Chem. Soc. 1998, 120, 3074; Tetrahedron 1997, 53, 17425; J. Chem. Soc., Chem. Commun. 1995, 15, 1515) and also dibenzothiophene-4,6-dicarboxylic acid [69747-72-4] and dibenzothiophene-4-carboxylic acid [2786-08-5] (obtained by carboxylating dibenzothiophene: Acta Pharm. Suec. 1978, 15, 337) can be reacted in a similar manner to Scheme 1 to give 4,6-difluorodibenzofuran, 4-fluorobenzofuran, 4,6-difluorobenzothiophene and 4-fluorodibenzothiophene (Scheme 2).

Metallation of 1,8-difluorofluorene in the 2- or 7-position or of 4,6-difluorodibenzofuran in the 3- or 7-position in a mixture of n-butyllithium and potassium tert-butoxide in THF at temperatures of ≦−70° C. (in a similar manner to Synlett 1990, 747), subsequent reaction with electrophiles (e.g. trimethyl borate, aldehydes, ketones, 4-n-alkylcyclohexanones, iodine, bromine), followed by reactions known to those skilled in the art of resulting, for example, 1,8-difluorofluorene-2-boronic acid, 1,8-difluorofluoren-2-ol or 2-(1-hydroxyalkyl) or 2-(1-hydroxycyclohexyl)-1,8-difluorofluorene provides various 1,8-difluorofluorenes substituted in the 2-position (Scheme 3).

Scheme 3

M = Li, K  a) n-BuLi/KOtBu/THF/hexane or n-BuLi/KOtBu/THF/hexane or sec-BuLi/THF/cyclohexane or LiTMP/THF/hexane  b) $R^1$-$CH_2$CHO 2. $H_3O^+$
c) 1. 4-TsOH/toluene 2. $H_2$/Pd-C/toluene  d) 1. B(OMe)$_3$ 2. $H_3O^+$  e) $H_2O_2$/MTBE
f) $R^1$(-$A^1$)$_m$-$CH_2$OH/DEAD/PPh$_3$/THF or $R^1$(-$A^1$)$_m$-$CH_2$Br/$K_2CO_3$/MEK
g) $R^1$(-$A^1$)$_m$-Hal/Pd(PPh$_3$)$_4$/Na$_2$CO$_3$/toluene/EtOH/H$_2$O  h) (F$_3$CSO$_2$)$_2$O/pyridine
i) $R^1$(-$A^1$)$_m$-B(OH)$_2$/Pd(PPh$_3$)$_4$/Na$_2$CO$_3$/toluene/EtOH/H$_2$O
k) R(-$A^1$)$_m$-C≡CH/Pd(PPh$_3$)$_2$Cl$_2$/CuI/NEt$_3$
l) H$_2$/Pd-C/THF k) $R^1$(-$A^1$)$_m$-C≡CH/Pd(PPh$_3$)$_2$Cl$_2$/CuI/NEt$_3$  l) H$_2$/Pd-C/ THF The Hal group is Cl, Br, I or OSO$_2$CF$_3$. In Schemes 4 to 7, the Rx group is the $R^1$(-$A^1$-$M^1$)$_m$ group or a suitable, optionally protected precursor thereof (for example Br or OSO$_2$CF$_3$ where Hal=I; benzyloxy; tetrahydropyranyloxy; tert-butyldiphenylsilanyloxy) which can be converted to this group in later steps by methods known per se and familiar to those skilled in the art.

1,8-Difluorofluorenes substituted in the 2-position by suitable $R^x$ and 4,6-difluorodibenzofurans substituted in the 3-position by suitable $R^x$ can be converted by metallation of the 7-position (in a similar manner to Synlett 1990, 747, ibid. 1991, 119, Tetrahedron Lett. 1996, 37, 6551) and subsequent reaction with electrophiles (e.g. trimethyl borate, DMF, CO$_2$, n-alkylaldehydes, 4-n-alkylcyclohexanones, iodine, bromine) to precursors from which the compounds of the formula (I) according to the invention can be prepared (Schemes 4 to 7).

Scheme 4

M = Li,
a) n-BuLi/THF/hexane or N-BuLi/KOtBu/THF/hexane or sec-BuLi/THF/cyclohexane or LiTMP/THF/hexane
b) 1. B(OMe)$_3$ 2. H$_3$O$^+$
c) I$_2$ (or Br$_2$)
d) 1. CO$_2$ 2. H$_3$O$^+$
e) 1. DMF 2. H$_3$O$^+$ M=Li, K a) n-BuLi/THF/hexane or n-BuLi/KOtBu/THF/hexane or sec-BuLi/THF/cyclohexane or LiTMP/THF/hexane b) 1. B(OMe)$_3$ 2. H$_3$O$^+$ c) I$_2$ (or Br$_2$) d) 1. CO$_2$ 2. H$_3$O$^+$ e) 1.DMF 2.H$_3$O$^+$ Scheme 5

-continued a) 1. B(OMe)$_3$ 2. H$_3$O$^+$  b) R$^2$-A$^2$-Hal/Pd(PPh$_3$)$_4$/Na$_2$CO$_3$/toluene/EtOH/H$_2$O
c) I$_2$ (or Br$_2$)  d) R$^2$-A$^2$-B(OH)$_2$/Pd(PPh$_3$)$_4$/Na$_2$CO$_3$/toluene/EtOH/H$_2$O
e) 1. 4-(R$^2$)-cyclohexanone. 2. H$_3$O$^+$ 3. 4-TsOH/toluene  f) H$_2$/Pd-C/THF
g) R$^2$-(A$^2$)$_n$-C≡CH/Pd(PPh$_3$)$_2$Cl$_2$/CuI/NEt$_3$

Scheme 6 a) H$_2$O$_2$/MTBE  b) R$^2$(-A$^2$)$_n$-CH$_2$OH/DEAD/PPh$_3$/THF or
R$^2$(-A$^2$)$_n$-CH$_2$Br/K$_2$CO$_3$/MEK  c) R$^2$(-A$^2$)$_n$-COOH/DCC/DMAP/CH$_2$Cl$_2$
d) (F$_3$CSO$_2$)$_2$O/pyridine  e) R$^2$(-A$^2$)$_n$-C≡CH/Pd(PPh$_3$)$_2$Cl$_2$/CuI/NEt$_3$
f) H$_2$/Pd-C/THF Scheme 7 a) $R^2(-A^2)_n$-OH/DCC/DMAP/CH$_2$Cl$_2$  b) LiAlH$_4$/THF 2. H$_3$O$^+$
c) $R^2(-A^2)_n$-OH/DEAD/PPh$_3$/THF  d) PBr$_3$/CHCl$_3$  e) PPh$_3$/xylene
f) $R^2(-A^2)_n$-CHO/KO$t$Bu/THF  g) $R^2(-A^2)_n$-CH$_2$P(Ph$_3$)Br/KO$t$Bu/THF
h) $R^2$-CH(CH$_2$OH)$_2$/4-TsOH/toluene  i) H$_2$/Pd-C/THF The preparation of the, for example alkyl-, alkenyl- or alkoxy-substituted, optionally additionally fluorinated benzoic acids, cyclohexanecarboxylic acids and phenylacetylenes (Schemes 3, 5 and 6), phenylboronic acids, pyridylboronic acids (Schemes 3 and 5), bromobenzenes, bromopyrimidines (Schemes 3 and 7), cyclohexanones (Scheme 5) and 2-alkylpropane-1,3-diols (Schemes 5 and 9) required for the syntheses of Schemes 3 to 7 and their reactions are known to those skilled in the art and are described, for example, in WO 96/00710, WO 96/30344, Liq. Cryst. 1995, 18, 1, Mol. Cryst. Liq. Cryst. 1991, 204, 43, Liq. Cryst. 1997, 23, 389, Synthesis 1996, 589, WO 92/11241, EP-A-0 665 825 and J. Mater. Chem. 1999, 9, 1669. Appropriately substituted benzyl alcohols and (hydroxymethyl)cyclohexanes $R^2$-A$^2$-CH$_2$OH can be obtained, for example, from the corresponding benzoic acids or cyclohexanecarboxylic acids $R^2$-A$^2$-COOH by reduction with lithium aluminum hydride (general procedure: Organikum, VEB Deutscher Verlag der Wissenschaften, 15th ed., Berlin 1984, Ch. 7.3.4). Their bromination with phosphorus tribromide (in a similar manner to J. Org. Chem. 1984, 49, 2534–2540) affords the benzyl bromides or (bromomethyl)cyclohexanes $R^2$-A$^2$-CH$_2$Br required in Scheme 5. Subsequent reaction with triphenylphosphine in xylene affords the triphenylphosphonium bromides $R^2$-A$^2$-CH$_2$-P(Ph$_3$)Br mentioned in Scheme 4. Appropriately substituted benzaldehydes and cyclohexanecarboxaldehydes R 2-A2-CHO are obtainable, for example, by reduction of the particular carboxylic ester $R^2$-A$^2$-COOR (Bull. Korean Chem. Soc. 1999, 20, 1373) or oxidation of the aforementioned benzyl alcohols and (hydroxymethyl)cyclohexanes $R^2$-A$^2$-CH$_2$OH (Tetrahedron Lett. 1968, 30, 3363).

Compounds of the formula (I) according to the invention having 1-cyclohexene-1,4-diyl or 2-fluoro-1-cyclohexene-1,4-diyl or 4-fluoro-3-cyclohexen-1-yl units are prepared as described in Liq. Cryst. 1997, 23, 69, DE-A-44 27 266, DE-A-196 07 996, DE-A-195 28 665 and EP-A-0 736 513. As far as the synthesis of specific $R^1$ and $R^2$ radicals is concerned, reference is made additionally, for example, to EP-A-0 355 008 (for compounds having silicon side chains), U.S. Pat. Nos. 4,798,680 (for optically active compounds having 2-fluoroalkyloxy units), EP-A-0 552 658 (for compounds having cyclohexylpropionic acid radicals) and EP-A-0 318 423 (for compounds having cyclopropyl groups in the side chain).

The synthesis of 9,9-difluorofluorene starting from fluorenone is described in J. Org. Chem. 1981, 46, 3917, J. Chem. Soc., Chem. Commun. 1995, 177, Synlett 1991, 191 and Tetrahedron 1996, 52, 9.

The invention is illustrated in detail by the examples which follow.

EXAMPLE 1

2-Butyloxy-1,8-difluorofluorene

A solution of 94 mmol of n-butyllithium (1.6 M solution in hexane) in 50 ml of dry tetrahydrofuran is cooled to ≦−70° C. and admixed dropwise under a protective gas atmosphere with a solution of 94 mmol of potassium tert-butoxide in 100 ml. of the same solvent. After stirring for 15-30 min, a solution of 78 mmol of 1,8-difluorofluorene in 200 ml of tetrahydrofuran is added dropwise at such a rate that the internal temperature is always below −70° C. Subsequently, stirring is continued at this temperature for another 2 h. A solution of 117 mmol of trimethyl borate in 100 ml of tetrahydrofuran is then added dropwise and the mixture is allowed to thaw gradually. The reaction mixture is admixed at −10° C. with 50 ml of water and acidified to pH I with concentrated hydrochloric acid. The phases are separated, the organic phase is washed with saturated sodium chloride solution and dried over sodium sulfate, and the solvent is removed under reduced pressure. 1,8-Difluorofluorene-2-boronic acid is obtained which is reacted further without purification.

40 ml of hydrogen peroxide (35 percent) is added dropwise at room temperature to a suspension of 54 mmol of 1,8-difluorofluorene-2-boronic acid in 120 ml of tert-butyl methyl ether and the mixture is subsequently heated to boiling for 4 h. After cooling, the mixture is admixed with 150 ml of water, the phases are separated and the organic phase is washed twice each with water and saturated sodium sulfite solution and also with saturated sodium chloride solution, so that no more peroxide can be detected. The organic phase is dried over sodium sulfate and the solvent is removed on a rotary evaporator. Recrystallization from heptane provides 1,8-difluorofluoren-2-ol.

56 mmol of 1-bromobutane are added to a mixture of 36 mmol of 1,8-difluorofluoren-2-ol and 109 mmol of anhydrous potassium carbonate in 250 ml of 2-butanone (methyl ethyl ketone) and the mixture is subsequently heated to reflux for 8 h. The still hot solution is then mixed with 50 ml of water. The phases are separated, the organic phase is washed with water and saturated sodium chloride solution and dried over sodium sulfate, and the solvent is removed on a rotary evaporator. The purification is effected by filtration through aluminum oxide (neutral) using toluene as the eluent and recrystallization from heptane. 2-Butoxy-1,8-difluorofluorene is obtained.

EXAMPLE 2

2-Butoxy- 1,8-difluoro-7-n-propylfluorene

The metallation of 23 mmol of 2-butoxy-1,8-difluorofluorene with 25 mmol of n-butyllithium (1.6 M solution in hexane) and 25 mmol of potassium tert-butoxide is effected in a similar manner to the procedure described in Example 1. 28 mmol mmol of propionaldehyde are subsequently added dropwise at ≦−70° C. and the mixture is allowed to thaw gradually. The reaction mixture is admixed at −10° C. with 50 ml of water and acidified to pH I using concentrated hydrochloric acid. The mixture is extracted using tert-butyl methyl ether, the combined organic phases are washed with saturated sodium chloride solution and dried over sodium sulfate, and the solvent is removed under reduced pressure. Chromatography on silica gel using dichloromethane as eluent provides 2-butoxy-1,8-difluoro-7-(1-hydroxypropyl) fluorene.

After the addition of approx. 0.5 g of 4-toluenesulfonic acid and a few drops of concentrated sulfuric acid, a solution of 14 mmol of 2-butoxy-1,8-difluoro-7-(1-hydroxypropyl) fluorene in 50 ml of toluene is heated on a water separator for 3 h. After cooling, the mixture is extracted using 5 percent sodium hydrogencarbonate solution and saturated sodium chloride solution and dried over sodium sulfate. Then 0.5 g of palladium catalyst (10 percent on activated carbon) are subsequently added and the mixture is hydrogenated at room temperature. The reaction mixture is filtered and the solvent is removed under reduced pressure. The crude product is purified by chromatography on silica gel and recrystallization from heptane. 2-Butoxy-1,8-difluoro-7-n-propylfluorene is obtained.

In a similar manner to Example 2, but using valeraldehyde, 4-n-propylcyclohexanone and 4-n-pentylcyclohexanone instead of propionaldehyde, it is possible to obtain:

EXAMPLE 3

2-Butoxy-1,8-difluoro-7-n-pentylfluorene

EXAMPLE 4

2-Butoxy-1,8-difluoro-7-(trans-4-n-propylcyclohexyl)fluorene

EXAMPLE 5

2-Butoxy-1,8-difluoro-7-(trans-4-n-pentylcyclohexyl)fluorene

EXAMPLE 6

2-Butoxy-1,8-difluoro-7-propyloxyfluorene

The metallation of 37 mmol of 2-butoxy-1,8-difluorofluorene (Example 1) with 41 mmol of n-butyllithium (1.6 M solution in hexane) and 41 mmol of potassium tert-butoxide is effected in a similar manner to the procedure described in Examples 1 and 2.45 mmol of trimethyl borate are subsequently added dropwise and the mixture is allowed to thaw gradually. The reaction mixture is admixed at −10° C. with water and acidified to pH 1 using concentrated hydrochloric acid. The phases are separated, the organic phase is washed with saturated sodium chloride solution and dried over sodium sulfate, and the solvent is removed under reduced pressure. 7-Butoxy-1,8-difluorofluorene-2-boric acid is obtained which is reacted further without purification.

The oxidation of 24 mmol of 7-butoxy-1,8-difluorofluorene-2-boronic acid with 22 ml of hydrogen peroxide (35 percent) in 60 ml of tert-butyl methyl ether is effected in a similar manner to the procedure described in Example 1. 7-Butoxy-1,8-difluorofluoren-2-ol is obtained.

The etherification of 9 mmol of 7-butoxy-1,8-difluorofluoren-2-ol with 12 mmol of 1-bromopropane and 27 mmol of potassium carbonate in 50 ml of acetone is effected in a similar manner to the procedure described in Example 1. Purification of the crude product by chromatography on silica gel (dichloromethane/heptane) and recrystallization from heptane provides 2-butoxy-1,8-difluoro-7-propyloxyfluorene.

In a similar manner to Example 6, but using 1-bromobutane and 1-bromohexane instead of 1-bromopropane, it is possible to obtain:

EXAMPLE 7

2,7-Dibutoxy-1,8-difluorofluorene

EXAMPLE 8

2-Butoxy-1,8-difluoro-7-n-hexyloxyfluorene

EXAMPLE 9

2-Butoxy-1,8-difluoro-7-(4-n-pentylphenyl)fluorene 12 mmol of 7-butoxy-1,8-difluorofluorene-2-boronic acid (Example 6, 1$^{st}$ stage), 20 ml of ethanol, a solution of 24 mmol of sodium carbonate in 20 ml of water and 1 mol % of tetrakis(triphenylphosphine)palladium(0) are added to a solution of 12 mmol of 4-n-pentylbromobenzene in 40 ml of toluene. The mixture is heated to boiling until the reaction is complete. After cooling, the mixture is admixed with 100 ml of water, the phases are separated and the aqueous phase is extracted with toluene. The combined organic phases are washed with saturated NaCl solution and dried over sodium sulfate, and the solvents are removed under reduced pressure. The crude product is chromatographed on silica gel (2:5 dichloromethane/heptane) and recrystallized from heptane. 2-Butoxy-1,8-difluoro-7-(4-n-pentylphenyl)fluorene is obtained.

In a similar manner to Example 9, but using 1-bromo-2-fluoro-4-n-pentylbenzene (Mol. Cryst. Liq. Cryst. 1991, 204, 43) and 1-bromo-2,3-difluoro-4-n-octyloxybenzene (obtained by brominating 2,3-difluoro-4-n-octyloxybenzene in a similar manner to Liq. Cryst. 1996, 20, 653), it is possible to obtain:

EXAMPLE 10

2-Butoxy-1,8-difluoro-7-(2-fluoro-4-n-pentylphenyl)fluorene

EXAMPLE 11

2-Butoxy-1,8-difluoro-7-(2,3-difluoro-4-n-octyloxyphenyl)fluorene

EXAMPLE 12

1,8-Difluoro-2-propylfluorene

The reaction of 1,8-difluorofluorene with propionaldehyde is effected in a similar manner to the procedure described in Example 2. 2-Propyl-1,8-difluorofluorene is obtained.

In a similar manner to Example 12, but using butyraldehyde and 4-n-propylcyclohexanone, it is possible to obtain:

EXAMPLE 13

2-Butyl-1,8-difluoropropylfluorene

EXAMPLE 15

1,8-Difluoro-2-(trans-4-n-propylcyclohexyl)fluorene

In a similar manner to Examples 2 and 3, but using 1,8-difluoro-2-propylfluorene (Example 12), 2-butyl-1,8-difluoropropylfluorene (Example 13) and 1,8-difluoro-2-(trans-4-n-propylcyclohexyl)fluorene (Example 13) instead of 2-butoxy-1,8-difluorofluorene (Example 1), it is possible to obtain:

EXAMPLE 16

1,8-Difluoro-2,7-dipropylfluorene

EXAMPLE 17

2-Butyl-1,8-difluoro-7-propylfluorene

EXAMPLE 18

1,8-Difluor-2-propyl-7-(trans-4-n-propylcyclohexyl)fluorene

In a similar manner to Example 1, but using 4,6-difluorodibenzofuran instead of 1,8-difluorofluorene and n-butyllithium instead of n-butyllithium/potassium tert-butoxide mixture, is obtained:

EXAMPLE 19

3-Butoxy-4,6-difluorobenzofuran

Starting from 3-butoxy-4,6-difluorodibenzofuran (Example 19) instead of 2-butyloxy-1,8-difluorofluorene (Example 1), it is possible in a similar manner to Examples 2 and 5 to obtain:

EXAMPLE 20

3-Butoxy-4,6-difluoro-7-n-propyldibenzofuran

EXAMPLE 21

3-Butoxy-4,6-difluoro-7-(trans-4-n-pentylcyclohexyl)dibenzofuran

In a similar manner to Example 12, but using 4,6-difluorodibenzofuran instead of 1,8-difluorofluorene and valeraldehyde instead of propionaldehyde, it is possible to obtain:

EXAMPLE 22

4,6-Difluoro-3-n-pentyldibenzofuran

In a similar manner to Example 16, but using 4,6-difluoro-3-n-pentyidibenzofuran (Example 22) instead of 1,8-difluoro-2-propylfluorene (Example 12) and valeraldehyde instead of propionaldehyde, it is possible to obtain:

EXAMPLE 23

4,6-Difluoro-3,7-di-n-pentyldibenzofuran

Application Example 1

A smectic C mixture consisting of

| | |
|---|---|
| 5-octyl-2-(4-octyloxyphenyl)pyrimidine | 19.42% |
| 5-octyloxy-2-(4-octyloxyphenyl)pyrimidine | 6.50% |
| 5-decyl-2-(4-octyloxyphenyl)pyrimidine | 15.44% |
| 5-octyloxy-2-(4-hexyloxyphenyl)pyrimidine | 13.11% |
| 5-octyloxy-2-(4-butyloxyphenyl)pyrimidine | 12.82% |
| 5-octyloxy-2-(4-decyloxyphenyl)pyrimidine | 12.61% |
| 5-octyl-2-(4-hexyloxyphenyl)pyrimidine | 20.10% | has a Δε value of dielectric anisotropy of +0.13; by adding 15% of the compound of Example 7, a value of Δε=−1.8 is achieved, so that the resulting mixture is suitable for the operation of a display in inverse mode (e.g. P. W. H. Surguy, Ferroelectrics 1991, 122, 63; or P. W. Ross, Proc. SID Conf. 1992, 217; or J. C. Jones et al., Displays 1993, Vol.14, No.2, pp. 86–93; or M. Koden, Ferroelectrics 1996, 179, 121).

Application Example 2

A chiral-smectic C mixture consisting of

| | |
|---|---|
| 2-(4-heptyloxyphenyl)-5-nonylpyrimidine | 19.6% |
| 5-nonyl-2-(4-octyloxyphenyl)pyrimidine | 19.6% |
| 5-nonyl-2-(4-nonyloxyphenyl)pyrimidine | 19.6% |
| 2-(2,3-difluoro-4-heptyloxyphenyl)-5-nonylpyrimidine | 6.5% |
| 2-(2,3-difluoro-4-octyloxyphenyl)-5-nonylpyrimidine | 6.5% |
| 2-(2,3-difluoro-4-nonyloxyphenyl)-5-nonylpyrimidine | 6.5% |
| 5-hexyloxy-2-(4-hexyloxyphenyl)pyrimidine | 19.6% |
| (S)-4-[4'-(2-fluorooctyloxy)biphenyl-4-yl]-1-heptylcyclohexanecarbonitrile | 2.0% | is admixed with 10% of the compound of Example 2.

Figure 1:
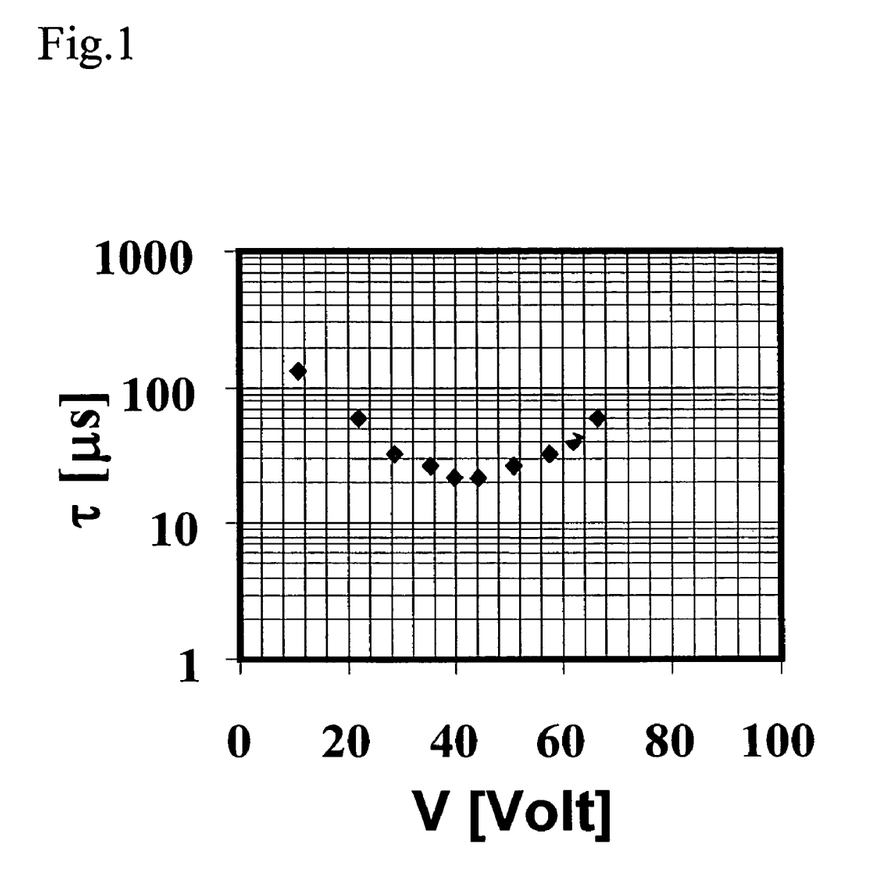
FIG. 1 shows the τVmin curve (τ plotted against the voltage) at Tc-30K, with monopolar pulses and a cell seperation of 1.3 μm.

This results in a mixture which, as revealed by FIG. 1, is suitable for the operation of displays in inverse mode, since the curve has the required minimum and the values lie within the technically relevant range.

What is claimed is:

1. A compound of the formula (I)

where

X is C=O,

Y is H or F $R^1$ and $R^2$ are the same or different and are each hydrogen, or are a straight-chain or branched alkyl radical having from 1 to 16 carbon atoms or a straight-chain or branched alkenyl radical having from 2 to 16 carbon atoms where a) one or more nonadjacent and nonterminal $CH_2$ groups may be replaced by —O—, —C(=O)O—, —O—C(=O)—, —O—C(=O)—O—, —C(=O)— or —Si(CH$_3$)$_2$—, and/or b) one $CH_2$ group may be replaced by —C≡C—, cyclopropane-1,2-diyl or cyclobutane-1,3-diyl, and/or c) one or more hydrogen atoms may be replaced by F or Cl, and/or d) the terminal $CH_3$ group may be replaced by one of the following chiral groups (optically active or racemic):

where $R^3$ is a straight-chain or branched alkyl radical having from 1 to 12 carbon atoms or a straight-chain or branched alkenyl radical having from 2 to 12 carbon atoms, in each of which one or more nonadjacent and nonterminal $CH_2$ groups may be replaced by —O— and/or one or more hydrogen atoms may be replaced by F or Cl, with the proviso where only one of $R^1$ and $R^2$ is a hydrogen, $M^1$ and $M^2$ are the same or different and are each —C(=O)—O—, —O—C(=O)—, —CH$_2$—O—, —O—CH$_2$—, —CF$_2$—O—, —O—CF$_2$—, —CH=CH—, —CF=CF—, —C≡C—, —CH$_2$—CH$_2$—C(=O)—O—, —O—C(=O)—CH$_2$—CH$_2$—, —CH$_2$—CH$_2$—, —CF$_2$—CF$_2$—, —(CH$_2$)$_4$— or a single bond, $A^1$ and $A^2$ are the same or different and are each 1,4-phenylene where one or two hydrogen atoms may be replaced by F, Cl or CN, pyridine-2,5-diyl where one hydrogen atom may be replaced by F, pyrimidine-2,5-diyl, 1,4-cyclohexylene where one or two hydrogen atoms may be replaced by CH$_3$ or F, 1-cyclohexene-1,4-diyl where one hydrogen atom may be replaced by CH$_3$ or F, or 1,3-dioxane-2,5-diyl, m and n are each independently 0 or 1, but in total not greater than 1.

2. A compound as claimed in claim 1, wherein, in formula (I),

X is C=O or O, $R^1$ and $R^2$ are the same or different and are each a straight-chain or branched alkyl radical having from 1 to 14 carbon atoms or a straight-chain or branched alkenyl radical having from 2 to 14 carbon atoms, in each of which one or more nonadjacent and nonterminal $CH_2$ groups may be replaced by —O— and/or one or more hydrogen atoms may be replaced by F,

$R^3$ is a straight-chain or branched alkyl radical having from 1 to 10 carbon atoms where one nonterminal $CH_2$ group may be replaced by —O—,

$M^1$ and $M^2$ are the same or different and are each —CH$_2$—O—, —O—CH$_2$—, —CH$_2$—CH$_2$— or a single bond,

$A^1$ and $A^2$ are the same or different and are each 1,4-phenylene where one or two hydrogen atoms may be replaced by F, or 1,4-cyclohexylene, and m and n are each independently 0 or 1, but in total not greater than 1.

3. A compound as claimed in claim 1, selected from the group of compounds of the formulae (I i) to (I q)

where
R[4] and R[5] are the same or different and are each a straight-chain alkyl, alkenyl or alkoxy radical having from 2 to 12 carbon atoms.

4. A compound as claimed in claim 3, selected from the group of compounds of the formulae (I i), (I k) and (I l) where R[4] and R[5] are the same or different and are each a straight-chain alkyl, alkenyl or alkoxy radical having from 2 to 10 carbon atoms.

5. A liquid-crystal mixture comprising one or more compounds as claimed in claim 1 in an amount of from 1 to 40% by weight, based on the liquid-crystal mixture.

6. The liquid-crystal mixture as claimed in claim 5, which is nematic or smectic.

7. The liquid-crystal mixture as claimed in claim 5, comprising at least three further components in addition to the compound or compounds of the formula (I).

8. A liquid-crystal display comprising a liquid-crystal mixture as claimed in claim 5.

9. The liquid-crystal display as claimed in claim 8, which comprises active matrix elements or is operated in inverse mode.

10. A compound which is 2-butyloxy-1,8-difluorofluorene.

* * * * *

UNITED STATES PATENT AND TRADEMARK OFFICE
CERTIFICATE OF CORRECTION

| | |
|---|---|
| PATENT NO. | : 7,018,685 B2 |
| APPLICATION NO. | : 10/466135 |
| DATED | : March 28, 2006 |
| INVENTOR(S) | : Wolfgang Schmidt et al. |

It is certified that error appears in the above-identified patent and that said Letters Patent is hereby corrected as shown below:

Column 23 line 41 reads "X is C=0," should read -- X is C=0, or 0 --

Signed and Sealed this

Twenty-fourth Day of June, 2008

JON W. DUDAS
*Director of the United States Patent and Trademark Office*